United States Patent [19]

Hughes

[11] Plant 4,451

[45] Aug. 21, 1979

[54] PEACH TREE WH215

[75] Inventor: J. Wilson Hughes, Monroeville, N.J.

[73] Assignee: Hilltop Orchards & Nurseries, Inc., Hartford, Mich.

[21] Appl. No.: 736,576

[22] Filed: Oct. 28, 1976

[51] Int. Cl.[2] ..... A01H 5/03

[52] U.S. Cl. ..... Plt./43

[58] Field of Search ..... Plt./43

*Primary Examiner*—Robert E. Bagwill

*Attorney, Agent, or Firm*—John R. Nesbitt

[57] ABSTRACT

A late-ripening peach tree bearing yellow-fleshed fruit which ships well and is non-browning.

1 Drawing Figure

1

This invention is a new and distinct variety of peach tree discovered by J. Wilson Hughes in a cultivated area in Sept., 1967, on the Knisel property, Haudingsville Road, Elk Township, County of Gloucester, N.J., behind the old packing house on the south side of the road.

The tree was propagated by bud grafting into young trees at the Hilltop Orchards & Nurseries, Inc., Hartford, Mich. and the unique characteristics of the peach tree have been maintained through asexual propagation. The specimens grown at Hilltop were assigned the experimental number of WH215, and the variety has been named "Sweet Sue".

The original tree, fruit and a branch with typical leaves are depicted in the enlarged color photograph that is part of this application. The Rio Oso Gem Peach Tree Variety is the assumed seed parent of the variety claimed and described hereafter.

TREE

Habit: Medium vigor, upright spreading, more vigorous than Rio Oso Gem which the entire tree closely resembles.

Disease Resistance: Good resistance to bacterial leafspot compared with Rio Oso Gem and the fruit and leaves are notably free of bacterial leafspot when compared with Rio Oso Gem.

LEAF

Typical peach leaf, resembles Rio Oso Gem.

FLOWER

Showy, the same as Rio Oso Gem.

2

FRUIT

Size and shape: Large, about $2\frac{1}{2}''$ diameter, same as Rio Oso Gem, with much smoother suture line, overall skin condition is normally more free of bacterial leafspot then the parent Rio Oso Gem.

Color: When compared with Rio Oso Gem, the fruit has a brighter yellow groundcolor, and a much brighter red overcolor, giving a mottled appearance. The color develops from distal (blossom) end of the fruit and the cheek is the typical speckled pinkish red of Rio Oso Gem and the back side fills in with striping and blotching of red. The red color is formed by many red dots or specks flowing together to appear as a blush, and the isolated dots are more apparent than on Rio Oso Gem because of the bright yellow groundcolor.

Pit Size: Small, being about $1\frac{5}{8}'' \times 1\frac{1}{8}'' \times \frac{7}{8}''$.

Flesh: Yellow with a red pit cavity which infiltrates into the flesh somewhat with considerable red in the suture line.

Skin: Smooth, almost no pubescence.

Texture: Very firm, somewhat coarse, melting.

Quality: Good, strong somewhat acid flavor.

Aroma: Very pleasant.

Maturity: Late season maturity, about two days later than Rio Oso Gem, very uniform ripening and very heavy early bearing.

Keeping Quality: Superior keeping and shipping quality.

Use: Used as a commercial shipping fresh market peach. Flesh is non-browning.

I claim:

1. A new and distinct variety of peach tree substantially as shown and described.

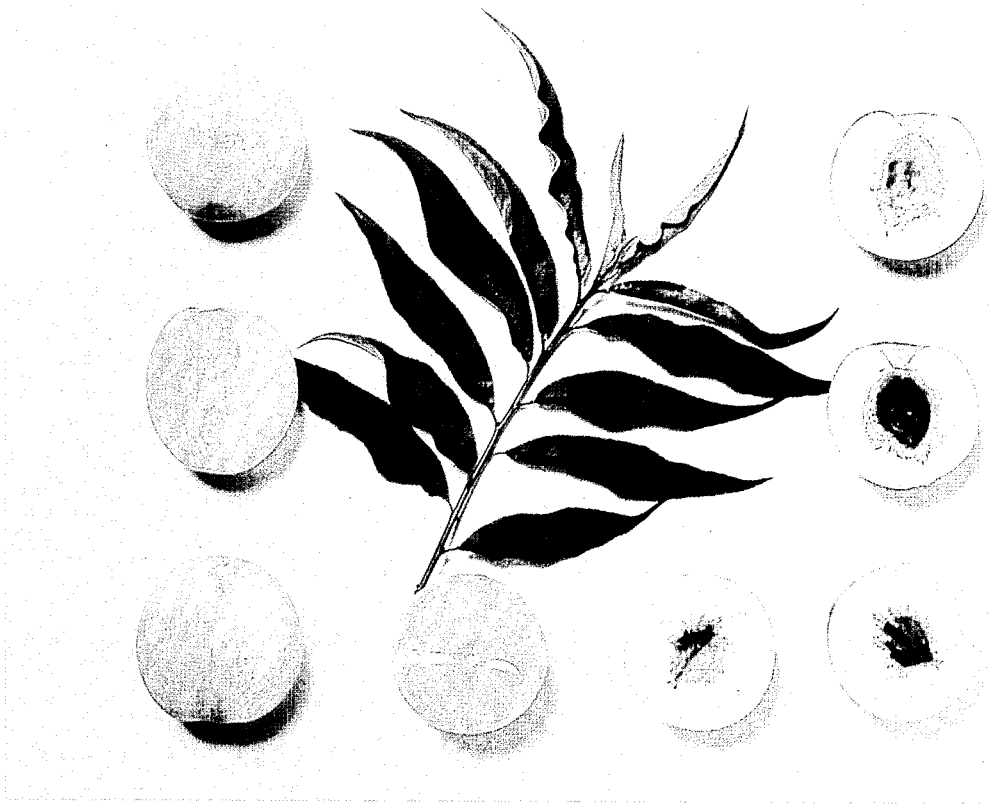
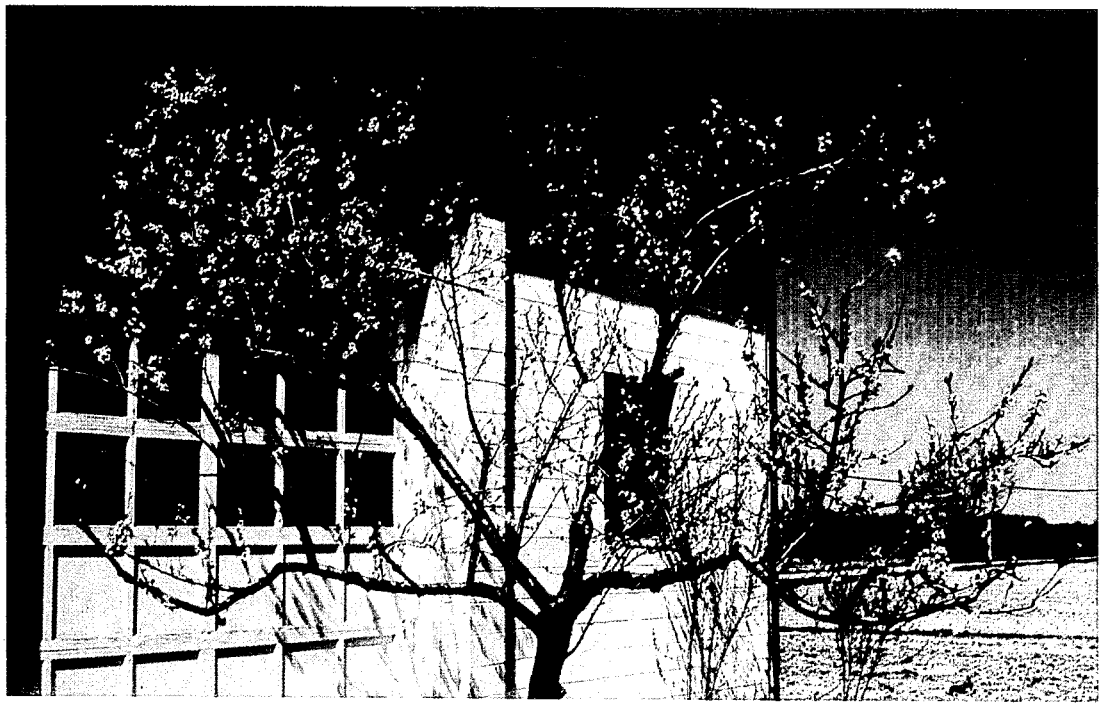

* * * * *